(12) United States Patent
Hao et al.

(10) Patent No.: US 9,750,702 B2
(45) Date of Patent: Sep. 5, 2017

(54) PHARMACEUTICAL COMPOSITION FOR TREATING PARKINSON'S DISEASE AND PREPARATION METHOD THEREOF

(75) Inventors: Weihua Hao, Taipei (TW); Jongjing Wang, Taipei (TW); Huiyun Chen, Taipei (TW)

(73) Assignee: INNOPHARMAX, INC., Taipei (TW)

( * ) Notice: Subject to any disclaimer, the term of this patent is extended or adjusted under 35 U.S.C. 154(b) by 0 days.

(21) Appl. No.: 13/518,767

(22) PCT Filed: Dec. 25, 2009

(86) PCT No.: PCT/CN2009/076069
§ 371 (c)(1),
(2), (4) Date: Jul. 19, 2012

(87) PCT Pub. No.: WO2011/075912
PCT Pub. Date: Jun. 30, 2011

(65) Prior Publication Data
US 2012/0276198 A1   Nov. 1, 2012

(51) Int. Cl.
| | |
|---|---|
| A61K 9/20 | (2006.01) |
| A61K 31/195 | (2006.01) |
| A61K 31/198 | (2006.01) |
| A61K 31/277 | (2006.01) |
| A61K 45/06 | (2006.01) |
| A61K 9/50 | (2006.01) |

(52) U.S. Cl.
CPC .......... *A61K 9/2077* (2013.01); *A61K 31/195* (2013.01); *A61K 31/198* (2013.01); *A61K 31/277* (2013.01); *A61K 45/06* (2013.01); *A61K 9/5084* (2013.01)

(58) Field of Classification Search
None
See application file for complete search history.

(56) References Cited

U.S. PATENT DOCUMENTS

| | | | |
|---|---|---|---|
| 2004/0048931 A1* | 3/2004 | Heacock et al. | 514/629 |
| 2006/0222703 A1 | 10/2006 | Politi | |
| 2009/0155369 A1* | 6/2009 | Huguet Riba et al. | 424/490 |
| 2010/0104634 A1* | 4/2010 | Kalantri | 424/452 |

FOREIGN PATENT DOCUMENTS

| | | |
|---|---|---|
| WO | WO 01/01984 A1 | 1/2001 |
| WO | WO 2008/053297 A2 | 5/2008 |
| WO | WO 2009/098661 A1 | 8/2009 |
| WO | WO 2009/098661 A1 | 8/2009 |

OTHER PUBLICATIONS

Skylighter. Skylighter products for making fireworks and pyrotechnics. Skylighter Inc. avaliable online from Mar. 30, 2013. [Retrieved from the internet on Oct. 30, 2013] <http://www.skylighter.com/fireworks/making-fireworks-projects/screen-mesh-metal-particle-size.asp>.*
International Search Report issued in PCT/CN2009/076069 mailed Oct. 8, 2010.

* cited by examiner

*Primary Examiner* — Johann R Richter
*Assistant Examiner* — Katherine Peebles
(74) *Attorney, Agent, or Firm* — Gary D. Colby; Dilworth Paxson, LLP (57) ABSTRACT

A pharmaceutical composition used to treat Parkinson's disease contains levodopa, carbidopa and entacapone or pharmaceutically acceptable salt thereof, and at least one kind of pharmaceutically acceptable excipients. Entacapone is not mixed with levodopa or carbidopa in the pharmaceutical composition. The preparation method of the pharmaceutical composition includes making the first particles with levodopa and carbidopa, making the second particles with entacapone, and then pressing the two kinds of particles into tablets.

22 Claims, 8 Drawing Sheets

PHARMACEUTICAL COMPOSITION FOR TREATING PARKINSON'S DISEASE AND PREPARATION METHOD THEREOF

FIELD OF THE INVENTION

The present invention is related to a pharmaceutical composition for treating Parkinson's disease and a method for preparing the above-mentioned pharmaceutical composition.

BACKGROUND OF THE INVENTION

Tablets made from a composition of levodopa and carbidopa are commonly used for treating Parkinson's disease. Carbidopa is an aromatic L-amino acid decarboxylase inhibitor, which can efficiently reduce the transformation of levodopa to dopamine and raise the concentration of levodopa and dopamine that function in the brain. This kind of medicine is commercially available in nowadays, for instance: Sinemet® sold by Bristol-Myers Squibb, Parcopa® sold by Schwarz Pharma and etc.

Besides, U.S. Pat. No. 5,446,194 also discloses a medicine, entacapone, for Parkinson's disease treatment. The medicine is a catechol-O-methyl transferase (COMT) inhibitor, which is used with levodopa to raise the concentration of levodopa in the brain and increase the bioavailability of levodopa by preventing levodopa from being metabolized to 3-methoxy-4-hydroxy-L-phenylalanine (3-OMD). Comtan® produced by Orion is such kind of medicine.

Patients can take a tablet comprising levodopa and carbidopa as well as a tablet containing entacapone several times a day to control their symptoms. However, it is a burden to patients with the symptom of dysphagia or tremor to take two tablets each time.

Thus, WO 01/01984 discloses a pharmaceutical composition comprising levodopa, carbidopa and entacapone, wherein carbidopa is not mixed with levodopa and entacapone substantially to increase the bioavailability of carbidopa. The composition can improve the compliance of patients by incorporating the three ingredients in one tablet. Currently, such combination is commercially available under the trade name Stalevo®, which is co-developed by Novartis and Orion.

To tailor treatment approaches for patients, Stalevo® is provided with various dosage strengths, such as Stalevo® 50, 75, 100, 125, 150 and 200. In all the dosage forms, entacapone is in a fixed amount of 200 mg, but the amount of carbidopa/levodopa is 12.5/50 mg, 18.75/75 mg, 25/100 mg, 31.25/125 mg, 37.5/150 mg and 50/200 mg, respectively. However, it is a very complicated process to manufacture various dosage forms with the disclosure of WO 01/01984. It is the reason that carbidopa is separated from levodopa and entacapone substantially according to WO 01/01984, it has to be granulated independently. On the other hand, levodopa and entacapone can be mixed for granulating; even so, it is still a complicated process to granulate the mixtures of the two ingredients because entacapone is in a fixed amount of 200 mg in all the dosage strengths, and the weight ratio of levodopa and entacapone is different in various dosage forms. Therefore, the processes to granulate the mixture of levodopa and entacapone have to be individually carried out for different dosage forms.

SUMMARY OF THE INVENTION

To better appreciate the aforementioned matters, the inventors have developed a novel manner to simplify the production procedure without influencing the dissolution rate of the active ingredients.

Therefore, one of the objectives of present invention is to provide a pharmaceutical composition for treating Parkinson's disease, which comprises levodopa, carbidopa and entacapone, or the pharmaceutically acceptable salts thereof; and at least one pharmaceutically acceptable excipient; wherein entacapone is not mixed with levodopa or carbidopa.

Another objective of present invention is to provide a pharmaceutical composition for treating Parkinson's disease, which at least comprises a first portion, a second portion and at least one pharmaceutically acceptable excipient; wherein said first portion comprises a mixture of levodopa and carbidopa, and said second portion comprises entacapone.

Another objective of present invention is to provide a method for preparing the aforesaid pharmaceutical composition, comprising the steps of:
(a) mixing levodopa, carbidopa and at least one first excipient to obtain a first mixture;
(b) granulating said first mixture to obtain a first granule;
(c) mixing entacapone and at least one second excipient to obtain a second mixture;
(d) granulating said second mixture to obtain a second granule;
(e) compressing the first granule and the second granule into a tablet.

To achieve the above objectives, the present invention provides a pharmaceutical composition for treating Parkinson's disease, which comprises 25 mg to 300 mg of levodopa; 5 mg to 75 mg of carbidopa; and 25 mg to 300 mg of entacapone; or the pharmaceutically acceptable salts thereof; and at least one pharmaceutically acceptable excipient; wherein entacapone is not mixed with levodopa or carbidopa.

In a preferable embodiment of present invention, said pharmaceutical composition is a solid oral pharmaceutical composition; preferably, a tablet; more preferably, a double-layer tablet; most preferably, one layer of said double-layer tablet comprises levodopa and carbidopa, and the other layer comprises entacapone.

In a preferable embodiment of present invention, said excipient is a binder, a diluent, a disintegrant, or a combination thereof; more preferably, said binder is microcrystalline cellulose, hydroxypropyl methylcellulose (HPMC), povidone, crospovidone, starch or a combination thereof; said diluent is microcrystalline cellulose, hydroxypropyl methylcellulose, sugar, mannitol, starch, or a combination thereof; said disintegrant is microcrystalline cellulose, hydroxypropyl methylcellulose, crospovidone, starch, or a combination thereof; most preferably, said excipient is microcrystalline cellulose.

In a preferable embodiment of present invention, said solid oral pharmaceutical composition further comprises a coating film.

The present invention also provides a pharmaceutical composition for treating Parkinson's disease, which at least comprises a first portion, a second portion and at least one pharmaceutically acceptable excipient; wherein said first portion comprises a mixture of levodopa and carbidopa, and said second portion comprises entacapone; preferably, said levodopa has an amount of 25 mg to 300 mg, carbidopa has an amount of 5 mg to 75 mg, and entacapone has an amount of 25 mg to 300 mg.

In a preferable embodiment of present invention, said pharmaceutical composition is an oral solid pharmaceutical composition; preferably, a tablet; more preferably, a double-layer tablet; most preferably, one layer of said double-layer tablet comprises levodopa and carbidopa, and the other layer comprises entacapone.

In a preferable embodiment of present invention, said excipient is a binder, a diluent, a disintegrant, or a combination thereof; more preferably, said binder is microcrystalline cellulose, hydroxypropyl methylcellulose, povidone, crospovidone, starch, or a combination thereof; said diluent is microcrystalline cellulose, hydroxypropyl methylcellulose, sugar, mannitol, starch, or a combination thereof; said disintegrant is microcrystalline cellulose, hydroxypropyl methylcellulose, crospovidone, starch, or a combination thereof. The Present invention also provides a method for preparing the aforesaid pharmaceutical composition, comprising the steps of:
 (a) mixing levodopa, carbidopa and at least one first excipient to obtain a first mixture;
 (b) granulating said first mixture to obtain a first granule;
 (c) mixing entacapone and at least one second excipient to obtain a second mixture;
 (d) granulating said second mixture to obtain a second granule;
 (e) compressing the first granule and second granule into a tablet.

In a preferable embodiment of present invention, said step (e) is compressing said first granules and said second granules into double-layer tablets; preferably, one layer of said double-layer tablet comprises levodopa and carbidopa, and the other layer comprises entacapone.

In a preferable embodiment of present invention, said excipient is a binder, a diluent, a disintegrant, or a combination thereof; more preferably, said binder is microcrystalline cellulose, hydroxypropyl methylcellulose, povidone, crospovidone, starch, or a combination thereof; said diluent is microcrystalline cellulose, hydroxypropyl methylcellulose, sugar, mannitol, starch, or a combination thereof; said disintegrant is microcrystalline cellulose, hydroxypropyl methylcellulose, crospovidone, starch, or a combination thereof; most preferably, said excipient is microcrystalline cellulose.

In a preferable embodiment of present invention, said granulating step is a wet granulation process.

In a preferable embodiment of present invention, said method further comprises the step after step (c), and the step comprises grinding said second mixture; preferably, said ground second mixture having a maximum diameter of about 250 μm; more preferably, said ground second mixture having a maximum diameter of about 150 μm.

In a preferable embodiment of present invention, said method further comprises the step of: sieving said ground second mixture; preferably, sieving said ground second mixture through a 60 to 100 mesh sieve; more preferably, sieving through a 100 mesh sieve.

In a prefer embodiment of present invention, said method further comprises the step after step (e), and the step comprises film-coating said compressed tablet.

To sum up, the present invention provides a pharmaceutical composition for treating Parkinson's disease, which comprises levodopa, carbidopa and entacapone, or the pharmaceutically acceptable salts thereof; and at least one pharmaceutically acceptable excipient; wherein entacapone is not mixed with levodopa or carbidopa.

The present invention provides a simplified process comparing to WO 01/01984. Carbidopa and levodopa, which is in a same weight ratio in all dosage forms, are prepared as a granule mixture. Moreover, entacapone, which is in a fixed amount in all dosage forms, is separately granulated. Therefore, it is easy to produce various dosage forms by just adjusting the amount of the granule mixture of carbidopa and levodopa. Also, the pharmaceutical composition of present invention has a dissolution profile similar to the conventional medicine for treating Parkinson's disease, Stalevo®.

DETAIL DESCRIPTION OF THE INVENTION

Except for the definition listed below, all the scientific terminologies should be explained as their original means, which is understood by those ordinary skilled in the art. If any argument is caused, the definitions in this specification shall be used as the major explanations.

The term "excipient" herein is referred as an inactive material that is used as a carrier for the active ingredients of a medicine; which comprises a binder, a diluent, a disintegrant, a lubricant, a compression aid agent, a preservative, a coating agent, a flavor, a color, a sweetener, etc.

The term"binder" herein is referred as a material used to combine ingredients of a medicine to provide mechanical strength. Examples thereof are microcrystalline cellulose, hydroxypropyl methylcellulose (HPMC), povidone, crospovidone, starch, or copolyvidone; wherein microcrystalline cellulose preferably is P101, P102, etc; hydroxypropyl methylcellulose (HPMC) can be low-substituted hydroxypropyl methylcellulose (HPMC-L) or high-substituted hydroxypropyl methylcellulose (HPMC-H), preferably high-substituted hydroxypropyl methylcellulose (HPMC-H), such as HPMC E5 LV, HPMC E15 LV, HPMC A15 LV, HPMC K3 Premium, etc; povidone preferably is K30, K15, K90, etc; starch preferably is corn starch or Starch 1500®; copolyvidone preferably is copolyvidone VA64.

The term "diluent" herein is referred as a material used to extend a tablet size that is convenient to use for patients. Examples thereof are microcrystalline cellulose, hydroxypropyl methylcellulose, dextrin, sugar, mannitol or starch; wherein microcrystalline cellulose preferably is P101, P102, etc; sugar preferably is lactose; starch preferably is corn starch.

The term "disintegrant" herein is referred as a material used to swell and dissolve a tablet when it is wet by water, and to break apart the tablet in digestive tract to release active ingredients. Examples thereof are microcrystalline cellulose, hydroxypropyl methylcellulose, croscarmellose sodium, crospovidone or starch; wherein microcrystalline cellulose preferably is P101, P102, etc; hydroxypropyl methylcellulose (HPMC) preferably is low-substituted hydroxypropyl methylcellulose (HPMC-L); starch preferably is corn starch or Starch 1500®.

The following examples are just the best exemplary embodiments, but not intend to limit the scope of present invention. Those ordinarily skilled in the art can make appropriate changes and amendments according to the disclosure of present invention without departing from the spirits of present invention.

EXAMPLES

Example 1

First, the ingredients listed in the following Table 1 were wet granulated to obtain granules containing levodopa and carbidopa: 1.4 mg of HPMC E5 LV was dissolved in the water to obtain a 5% HPMC E5 LV solution. Then, the remained HPMC E5 LV, carbidopa monohydrate, levodopa and mannitol were sequentially and evenly mixed to obtain a first mixture. After that, said first mixture and said 5% HPMC E5 LV solution were sequentially put into a granulator to granulate. The resulted granules were sieved through a 25 mesh sieve and then dried in a 50° C. oven until the water content thereof is between the range of 1%-3%. A first granule is therefore obtained.

TABLE 1

| ingredients | Weight (mg) |
| --- | --- |
| Levodopa | 100.00 |
| Carbidopa monohydrate | 27.00 |
| mannitol | 88.00 |
| HPMC E5 LV | 6.40 |
| Total weight | 221.40 |

Next, the ingredients listed in the following Table 2 were wet granulated to obtain granules containing entacapone: 2.55 mg of HPMC E5 LV was dissolved in the water to obtain a 5% HPMC E5 LV solution. Then, the remained HPMC E5 LV, microcrystalline cellulose, SDS, mannitol and entacapone were sequentially and evenly mixed to obtain a second mixture. After that, said second mixture and said 5% HPMC E5 LV solution were sequentially put into a granulator to granulate. The resulted granules were sieved through a 25 mesh sieve and then dried in a 50° C. oven until the water content thereof is between the range of 1%-3%. A second granule is therefore obtained.

TABLE 2

| ingredients | weight (mg) |
| --- | --- |
| Entacapone | 200.00 |
| microcrystalline cellulose | 0.50 |
| mannitol | 88.00 |
| HPMC E5 LV | 7.55 |
| SDS | 11.00 |
| Total weight | 307.05 |

Last, tablets were prepared according to the ingredients listed in the following Table 3: said first granules containing levodopa and carbidopa and said second granules containing entacapone were mixed, and then mixed with crospovidone and magnesium stearate and compressed into tablets.

TABLE 3

| ingredients | weight (mg) |
| --- | --- |
| First granule | 221.40 |
| Second granule | 307.05 |
| crospovidone | 10.00 |
| magnesium stearate | 5.00 |
| Total weight | 543.45 |

Dissolution Test

Dissolution rate is a key parameter for bioequivalence of medicines containing the same active ingredients. A medicine having good dissolution rate indicates that said medicine is able to be disintegrated, dissolved and released appropriately in digestive tract and therefore absorbed by human body.

The following tests were conducted, and the dissolution profiles of levodopa, carbidopa and entacapone of said obtained tablet in the period of 120 minutes were monitored.

(1). Dissolution test for levodopa/carbidopa

The dissolution test was referred to the dissolution method of Levodopa/Carbidopa/Entacapone listed in the United States Pharmacopeia (USP 32, NF27 (1791)) and the Dissolution Methods Database on FDA website. The dissolution test was conducted by using the USP standard basket with a rotation speed of 50 rpm. The medium was 750 mL 0.1 N HCL solution, but the period of test was changed to 120 minutes. After that, HPLC analysis was carried out. The medicine for treating Parkinson's disease, Stalevo®, containing levodopa, carbidopa and entacapone, was used as a reference product in this test.

(2). Dissolution test for entacapone

The dissolution test was referred to the dissolution method of Levodopa/Carbidopa/Entacapone listed in the Dissolution Methods Database on FDA website. The dissolution test was conducted by using the USP standard basket with a rotation speed of 125 rpm. The medium was 900 mL phosphate buffer solution, pH 5.5, and the period of test was changed to 120 minutes. After that, HPLC analysis was carried out. Stalevo® was used as a reference product in this test.

Figure 1:
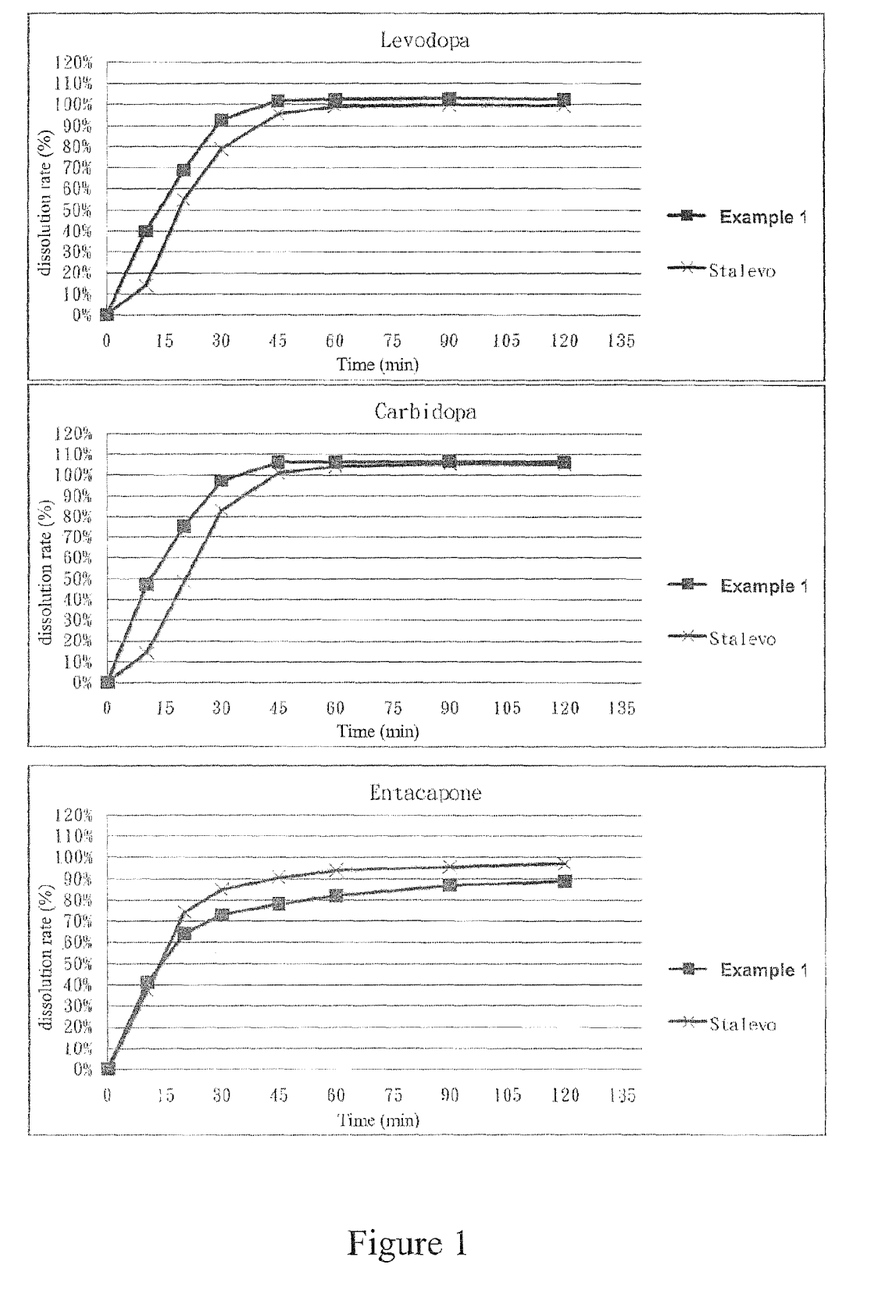
FIG. 1 shows the dissolution profiles of levodopa, carbidopa and entacapone of the tablet obtained from Example 1 in the period of 120 minutes, wherein the reference product is Stalevo®.

Dissolution tests were conducted, and the dissolution profiles of levodopa, carbidopa and entacapone of said obtained tablet in the period of 120 minutes were monitored, wherein Stalevo® was used as a reference product. The result is shown in FIG. 1, wherein the dissolution profiles of levodopa, carbidopa and entacapone are very similar to that of the reference product.

Example 2

First, the ingredients listed in the following Table 4 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator to granulate. The resulted granules were sieved through a 25 mesh sieve and then dried in a 50° C. oven until the water content thereof is between the range of 1%-3%. A first granule is therefore obtained.

TABLE 4

| ingredients | weight (mg) |
| --- | --- |
| Levodopa | 100.00 |
| Carbidopa monohydrate | 27.00 |
| mannitol | 88.00 |
| HPMC E5 LV | 6.40 |
| Total weight | 221.40 |

Next, the ingredients listed in the following Table 5 were wet granulated to obtain granules containing entacapone: microcrystalline cellulose, SDS, mannitol, PVP K30 and entacapone were sequentially and evenly mixed to obtain a second mixture. After that, said second mixture was introduced into a grinding machine and ground. The ground powder was then sieved through a 100 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 5

| ingredients | weight (mg) |
| --- | --- |
| Entacapone | 200.00 |
| microcrystalline cellulose | 0.50 |
| mannitol | 88.00 |
| PVP K30 | 120.00 |
| SDS | 20.00 |
| Total weight | 428.50 |

Last, tablets were prepared according to the ingredients listed in the following Table 6: said first granules containing levodopa and carbidopa and said second granules containing entacapone were mixed first, and then mixed with crospovidone and magnesium stearate and compressed into tablets.

TABLE 6

| ingredients | weight (mg) |
| --- | --- |
| first granule | 221.40 |
| second granule | 428.50 |
| crospovidone | 10.00 |
| magnesium stearate | 5.00 |
| Total weight | 664.90 |

Figure 2:
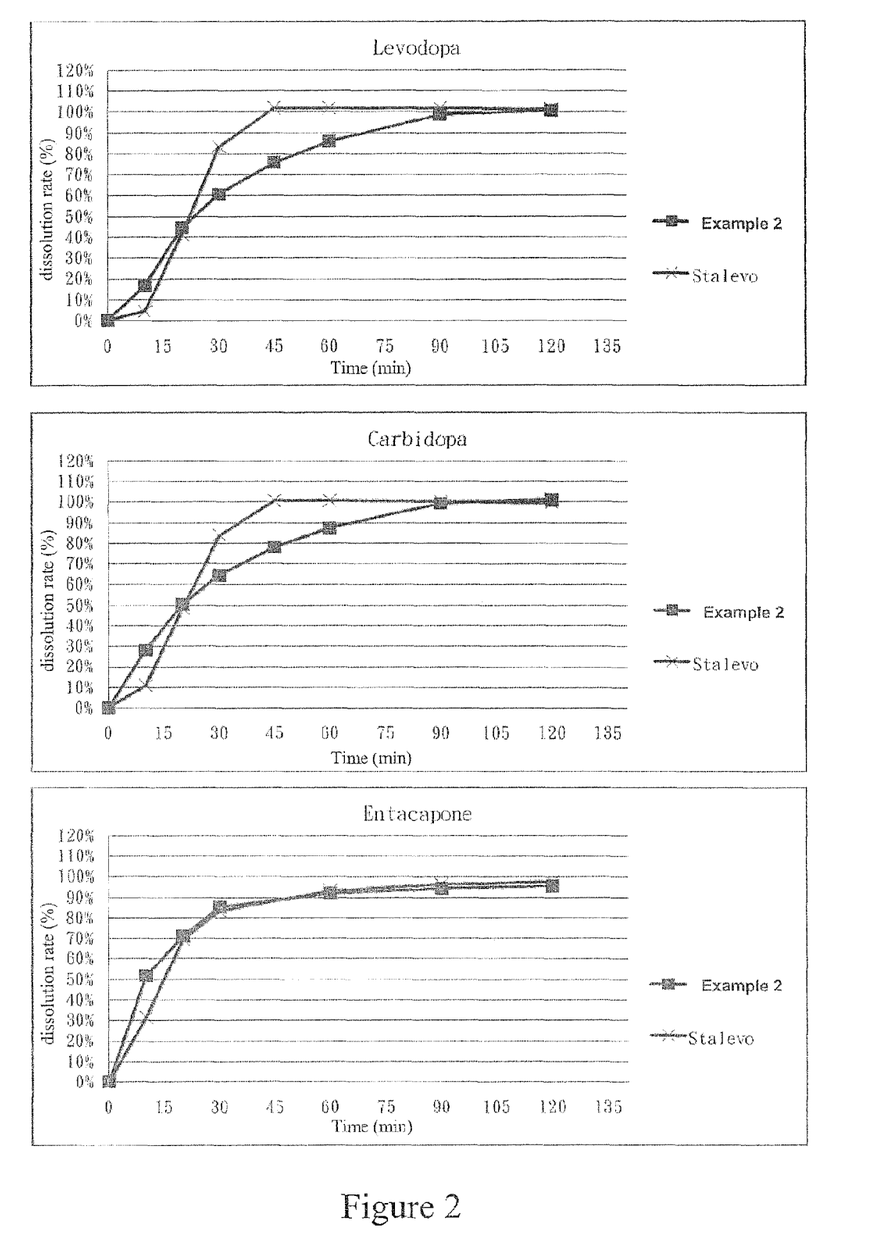
FIG. 2 shows the dissolution profiles of levodopa, carbidopa and entacapone of the tablet obtained from Example 2 in the period of 120 minutes, wherein the reference product is Stalevo®.

Dissolution tests were conducted according to Example 1 and the dissolution profiles of levodopa, carbidopa and entacapone of said tablets in the period of 120 minutes were monitored, wherein Stalevo® was used as a reference product. The result is shown in FIG. 2, wherein the dissolution rates of levodopa and carbidopa are very similar to that of the reference product; and dissolution profiles of entacapone are almost the same as that of reference product.

Example 3

First, the ingredients listed in the following Table 7 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator to granulate. The resulted granules were sieved through a 25 mesh sieve and then dried in a 50° C. oven until the water content thereof is between the range of 1%-3%. A first granule is therefore obtained.

TABLE 7

| ingredients | weight (mg) |
| --- | --- |
| Levodopa | 100.00 |
| Carbidopa monohydrate | 27.00 |
| mannitol | 88.00 |
| HPMC E5 LV | 6.40 |
| Total weight | 221.40 |

Next, the ingredients listed in the following Table 8 were wet granulate to obtain granules containing entacapone: microcrystalline cellulose, SDS, PVP K30, mannitol and entacapone were sequentially and evenly mixed to obtain a second mixture. After that, said second mixture was introduced into a grinding machine and ground. The ground powder was then sieved through a 100 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 8

| Ingredients | weight (mg) |
| --- | --- |
| Entacapone | 200.00 |
| microcrystalline cellulose | 0.50 |
| Mannitol | 168.00 |
| PVP K30 | 40.00 |
| SDS | 12.00 |
| Total weight | 420.50 |

Last, tablets were prepared according to the ingredients listed in the following Table 9: said first granules containing levodopa and carbidopa were mixed with 5 mg of crospovidone and 1.7 mg of magnesium stearate to obtain a first mixture; said second granules containing entacapone were mixed with 5 mg of crospovidone and 3.4 mg of magnesium stearate to obtain a second mixture; then, said first mixture and said second mixture were compressed into double-layer tablets.

TABLE 9

| Ingredients | weight (mg) |
| --- | --- |
| first granule | 221.40 |
| second granule | 420.50 |
| Crospovidone | 10.00 |
| magnesium stearate | 5.10 |
| Total weight | 657.00 |

Dissolution tests were conducted according to Example 1, and the dissolution profiles of levodopa, carbidopa and entacapone of said tablets in the period of 120 minutes were monitored, wherein Stalevo® was used as a reference product.

Figure 3:
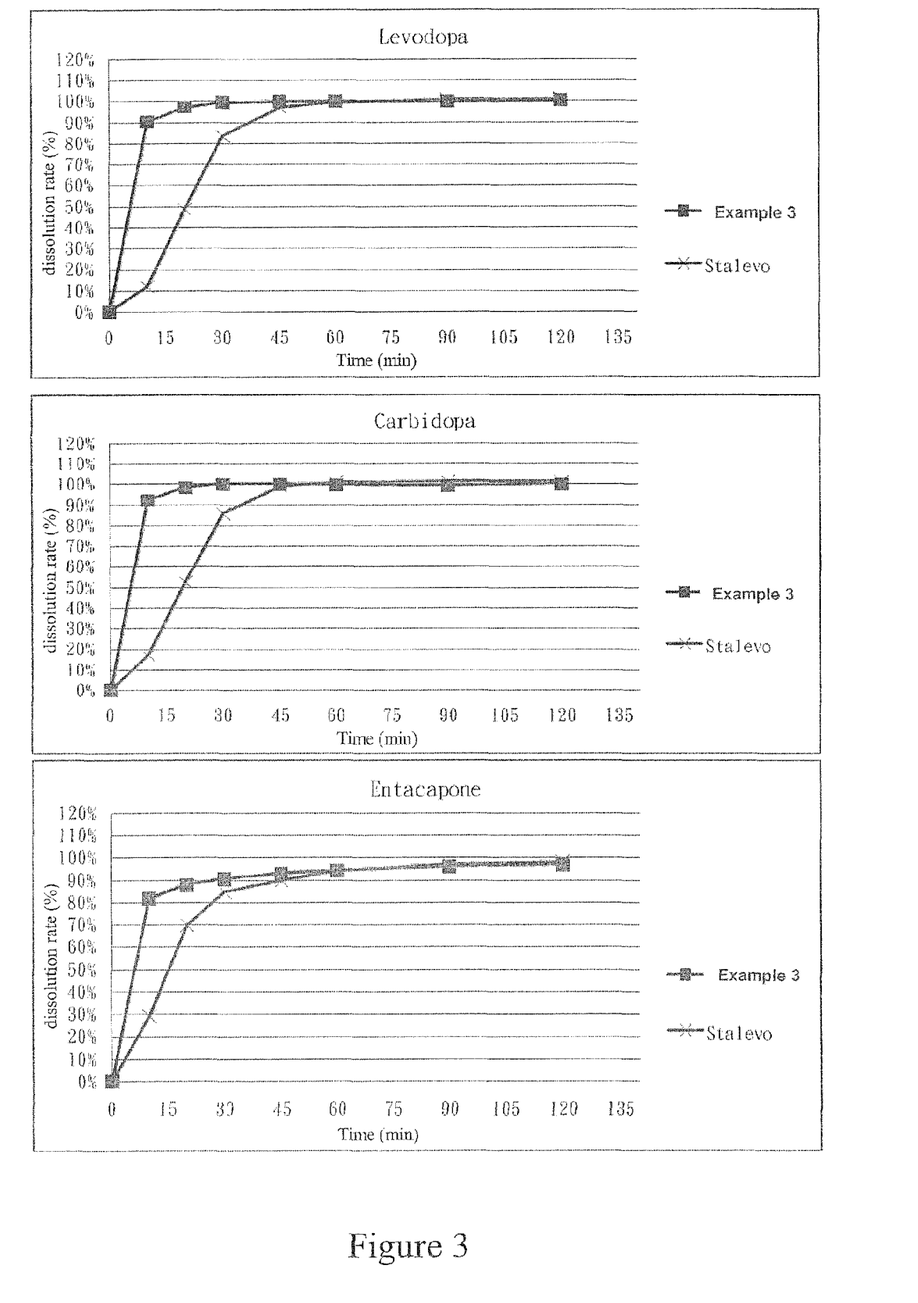
FIG. 3 shows the dissolution profiles of levodopa, carbidopa and entacapone of the tablet obtained from Example 3 in the period of 120 minutes, wherein the reference product is Stalevo®.

The result is shown in FIG. 3, wherein the dissolution rates of levodopa, carbidopa and entacapone are a little faster than that of reference product initially, but they are almost the same as that of reference product after 45 minutes.

Example 4

First, the ingredients listed in the following Table 10 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator to granulate. The resulted granules were sieved through a 25 mesh sieve and then dried in a 50° C. oven until the water content thereof is between the range of 1%-3%. A first granule is therefore obtained.

TABLE 10

| ingredients | weight(mg) |
| --- | --- |
| Levodopa | 100.00 |
| Carbidopa monohydrate | 27.00 |
| mannitol | 88.00 |
| HPMC E5 LV | 16.40 |
| Total weight | 231.40 |

Next, the ingredients listed in the following Table 11 were wet granulated to obtain granules containing entacapone: microcrystalline cellulose, SDS, PVP K30, mannitol and entacapone were sequentially and evenly mixed to obtain a second mixture. After that, said second mixture was introduced into a grinding machine and ground. The ground powder was then sieved through a 100 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 11

| ingredient | weight(mg) |
| --- | --- |
| Entacapone | 200.00 |
| microcrystalline cellulose | 0.50 |
| mannitol | 168.00 |
| PVP K30 | 40.00 |
| SDS | 12.00 |
| Total weight | 420.50 |

Last, tablets were prepared according to the ingredients listed in the following Table 12: said first granules containing levodopa and carbidopa were mixed with 1.7 mg of magnesium stearate to obtain a first mixture; said second granules containing entacapone were mixed with 5 mg of crospovidone and 3.4 mg of magnesium stearate to obtain a second mixture; then, said first mixture and said second mixture were compressed into double-layer tablets.

TABLE 12

| ingredients | weight(mg) |
| --- | --- |
| first granule | 231.40 |
| second granule | 420.50 |
| crospovidone | 5.00 |
| magnesium stearate | 5.10 |
| Total weight | 662.00 |

Figure 4:
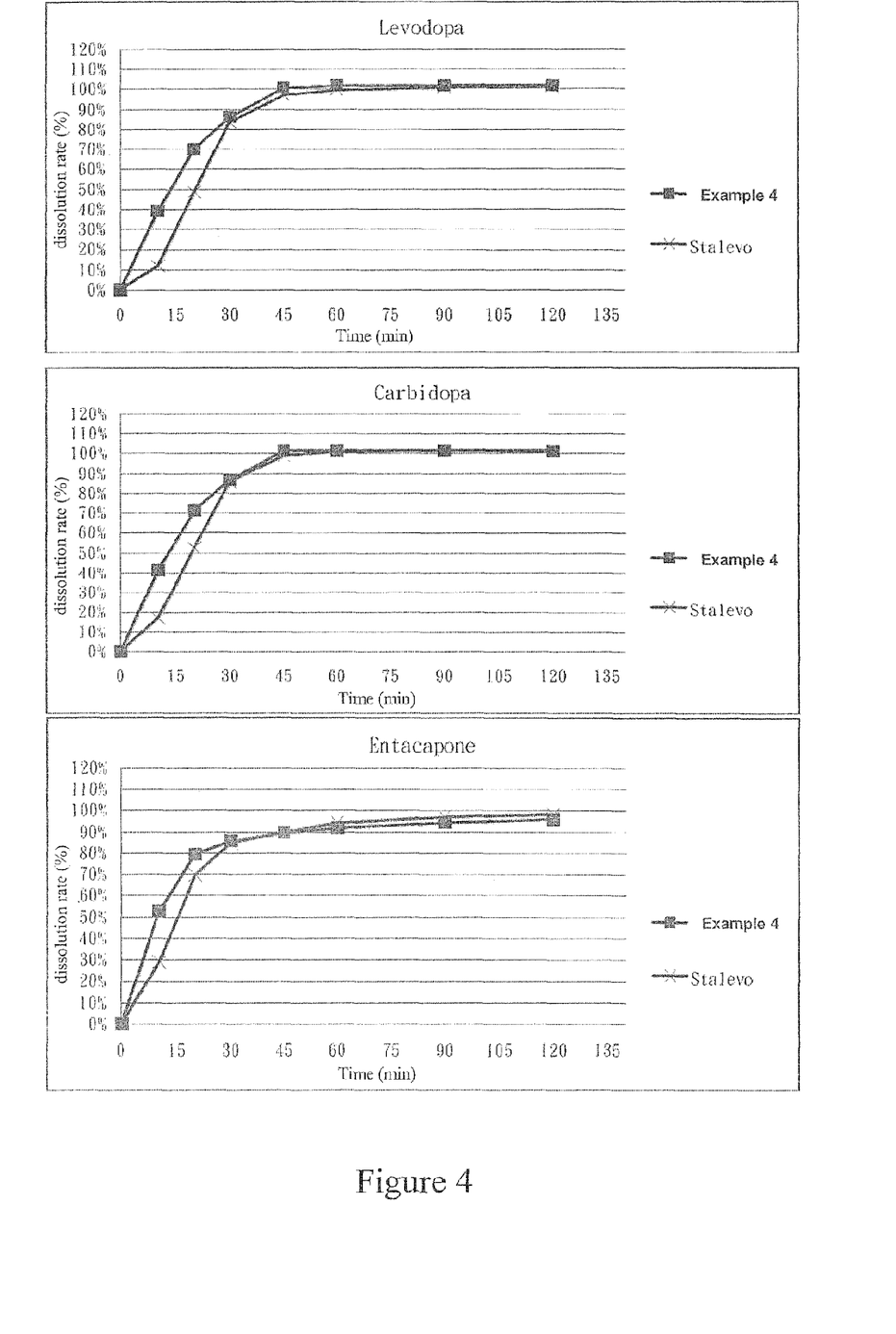
FIG. 4 shows the dissolution profiles of levodopa, carbidopa and entacapone of the tablet obtained from Example 4 in the period of 120 minutes, wherein the reference product is Stalevo®.

Dissolution tests were conducted according to Example 1, and the dissolution profiles of levodopa, carbidopa and entacapone of said tablets in the period of 120 minutes were monitored, wherein Stalevo® was used as a reference product. The result is shown in FIG. 4, wherein the dissolution profiles of levodopa, carbidopa and entacapone are very similar to that of the reference product.

Example 5

First, the ingredients listed in the following Table 13 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator and granulated. The resulted granules were sieved through a 25 mesh sieve and then dried in a 50° C. oven until the water content thereof is between the range of 1%-3%. A first granule is therefore obtained.

TABLE 13

| ingretients | weight(mg) |
| --- | --- |
| Levodopa | 100.00 |
| Carbidopa monohydrate | 27.00 |
| mannitol | 88.00 |
| HPMC E5 LV | 16.40 |
| Total weight | 231.40 |

Next, the ingredients listed in the following Table 14 were wet granulated to obtain granules containing entacapone: microcrystalline cellulose, SDS, mannitol, PVP K30, and entacapone were sequentially and evenly mixed to obtain a second mixture. After that, said second mixture was introduced into a grinding machine and ground. The ground powder was then sieved through a 100 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 14

| ingredients | weight(mg) |
| --- | --- |
| Entacapone | 200.00 |
| microcrystalline cellulose | 0.50 |
| mannitol | 168.00 |
| PVP K30 | 40.00 |
| SDS | 12.00 |
| Total weight | 420.50 |

Last, tablets were prepared according to the ingredients listed in the following Table 15: said first granules containing levodopa and carbidopa were mixed with 1.7 mg of magnesium stearate to obtain a first mixture; said second granules containing entacapone were mixed with 5 mg of crospovidone and 3.4 mg of magnesium stearate to obtain a second mixture; said first mixture and said second mixture were compressed into double-layer tablets; then said tablets were coated by Opadry AMB to increase its weight by 4%.

TABLE 15

| Ingredients | weight(mg) |
| --- | --- |
| first granule | 231.40 |
| second granule | 420.50 |
| crospovidone | 5.00 |
| magnesium stearate | 5.10 |
| Opadry AMB | 26.48 |
| Total weight | 688.48 |

Figure 5:
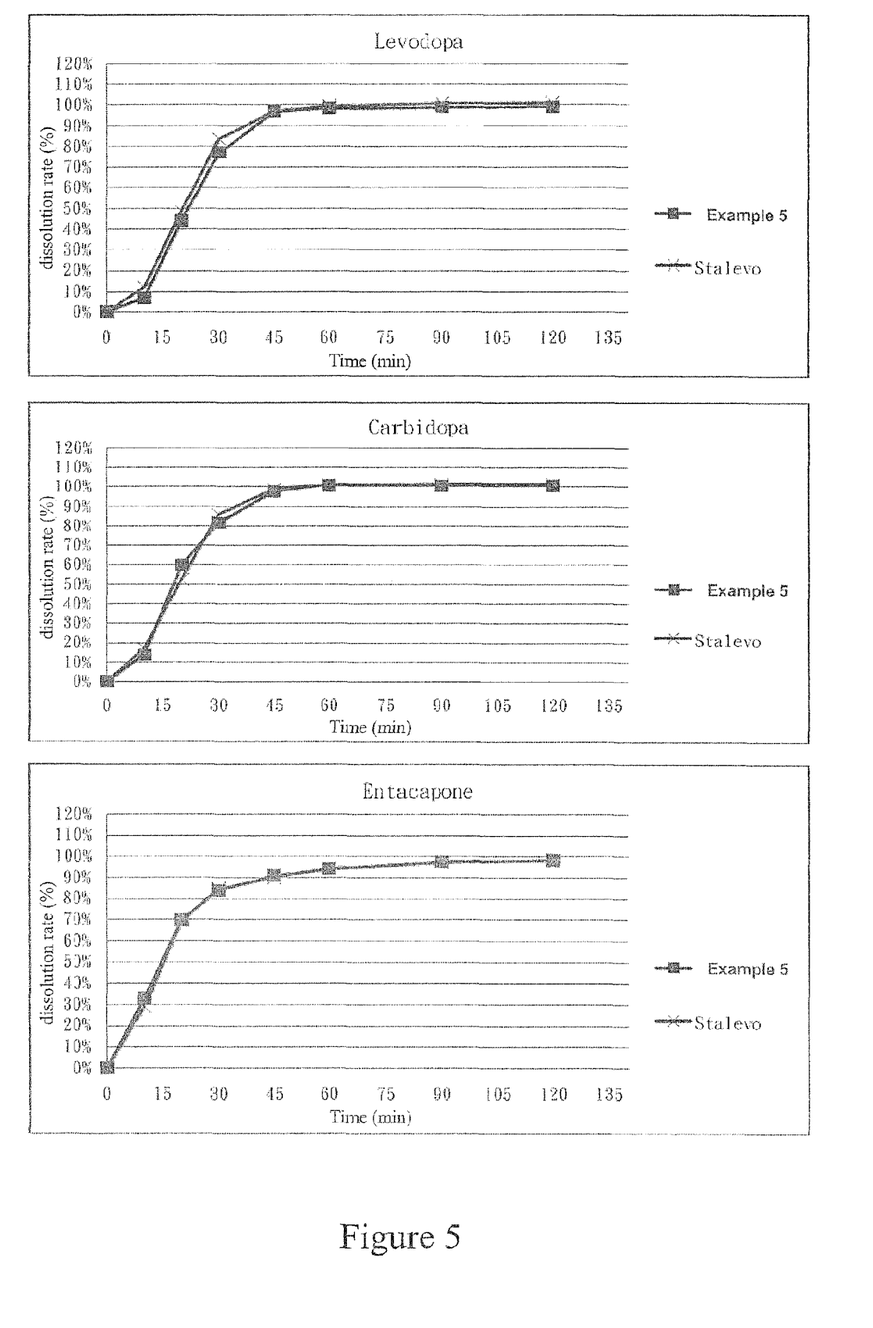
FIG. 5 shows the dissolution profiles of levodopa, carbidopa and entacapone of the tablet obtained from Example 5 in the period of 120 minutes, wherein the reference product is Stalevo®.

Dissolution tests were conducted according to Example 1, and the dissolution profiles of levodopa, carbidopa and entacapone of said tablets in the period of 120 minutes were monitored, wherein Stalevo® was used as a reference product. The result is shown in FIG. 5, wherein the dissolution rates of levodopa, carbidopa and entacapone are almost as same as that of the reference product.

Example 6

First, the ingredients listed in the following Table 16 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator and granulated. The resulted granules were sieved through a 25 mesh sieve and then dried in a 50° C. oven until the water content thereof is between the range of 1%-3%. A first granule is therefore obtained.

TABLE 16

| ingredients | weight(mg) |
| --- | --- |
| Levodopa | 100.00 |
| Carbidopa monohydrate | 27.00 |

TABLE 16-continued

| ingredients | weight(mg) |
| --- | --- |
| mannitol | 88.00 |
| HPMC E5 LV | 16.40 |
| Total weight | 231.40 |

Next, the ingredients listed in the following Table 17 were wet granulated to obtain granules containing entacapone: microcrystalline cellulose, SDS, PVP K30, mannitol and entacapone was sequentially and evenly mixed to obtain a second mixture. After that, said second mixture was introduced into a grinding machine and ground. The ground powder was then sieved through a 60 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 17

| ingredients | weight(mg) |
| --- | --- |
| Entacapone | 200.00 |
| microcrystalline cellulose | 0.50 |
| mannitol | 168.00 |
| PVP K30 | 40.00 |
| SDS | 12.00 |
| Total weight | 420.50 |

Last, tablets were prepared according to the ingredients listed in the following Table 18: said first granules containing levodopa and carbidopa were mixed with 1.7 mg of magnesium stearate to obtain a first mixture; said second granules containing entacapone were mixed with 5 mg of crospovidone and 3.4 mg of magnesium stearate to obtain a second mixture; then, said first mixture and said second mixture were compressed into double-layer tablets.

TABLE 18

| ingredients | weight(mg) |
| --- | --- |
| first granule | 231.40 |
| second granule | 420.50 |
| crospovidone | 5.00 |
| magnesium stearate | 5.10 |
| Total weight | 662.00 |

Figure 6:
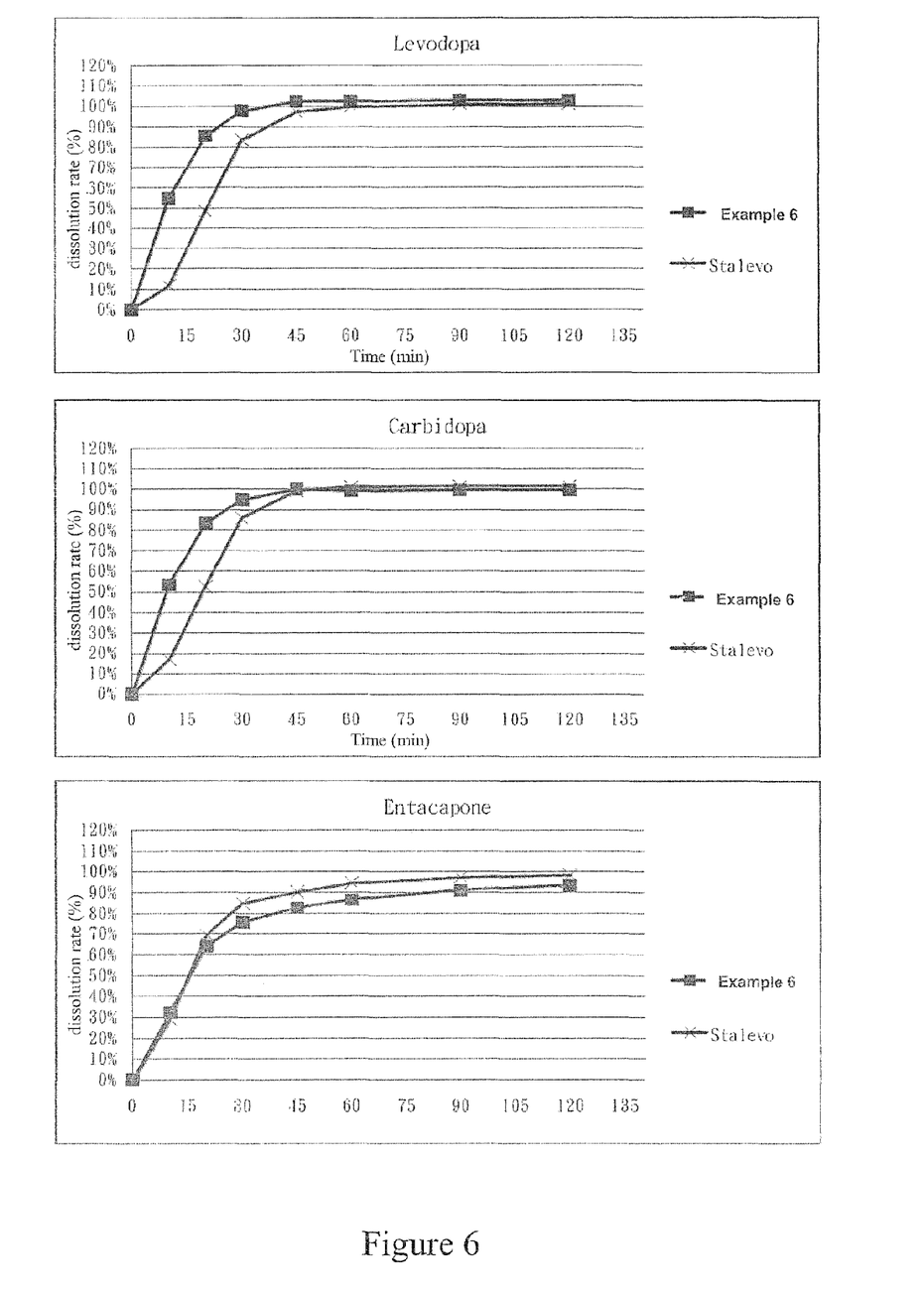
FIG. 6 shows the dissolution profiles of levodopa, carbidopa and entacapone of the tablet obtained from Example 6 in the period of 120 minutes, wherein the reference product is Stalevo®.

Dissolution tests were conducted according to Example 1, and the dissolution profiles of levodopa, carbidopa and entacapone of said tablets in the period of 120 minutes were monitored, wherein Stalevo® was used as a reference product. The result is shown in FIG. 6, wherein the dissolution amounts levodopa, carbidopa and entacapone are very similar to that of the reference product.

Example 7

First, the ingredients listed in the following Table 19 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5

LV solution were sequentially introduced into a granulator and granulated. The resulted granules were sieved through a 25 mesh sieve and then dried in a 50° C. oven until the water content thereof is between the range of 1%-3%. A first granule is therefore obtained.

TABLE 19

| ingredients | weight(mg) |
| --- | --- |
| Levodopa | 100.00 |
| Carbidopa monohydrate | 27.00 |
| mannitol | 88.00 |
| HPMC E5 LV | 16.40 |
| Total weight | 231.40 |

Next, the ingredients listed in the following Table 20 were wet granulated to obtain granules containing entacapone: microcrystalline cellulose, SDS, PVP K30, mannitol and entacapone were sequentially and evenly mixed to obtain a second mixture. After that, said second mixture was introduced into a grinding machine and ground. The ground powder was then sieved through a 80 mesh sieve and put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 20

| Ingredients | weight(mg) |
| --- | --- |
| Entacapone | 200.00 |
| microcrystalline cellulose | 0.50 |
| Mannitol | 168.00 |
| PVP K30 | 40.00 |
| SDS | 12.00 |
| Total weight | 420.50 |

Last, tablets were prepared according to the ingredients listed in the following Table 21: said first granules containing levodopa and carbidopa were mixed with 1.7 mg of magnesium stearate to obtain a first mixture; said second granules containing entacapone were mixed with 5 mg of crospovidone and 3.4 mg of magnesium stearate to obtain a second mixture; then, said first mixture and said second mixture were compressed into double-layer tablets.

TABLE 21

| Ingredients | weight(mg) |
| --- | --- |
| first granule | 231.40 |
| second granule | 420.50 |
| Crospovidone | 5.00 |
| magnesium stearate | 5.10 |
| Total weight | 662.00 |

Figure 7:
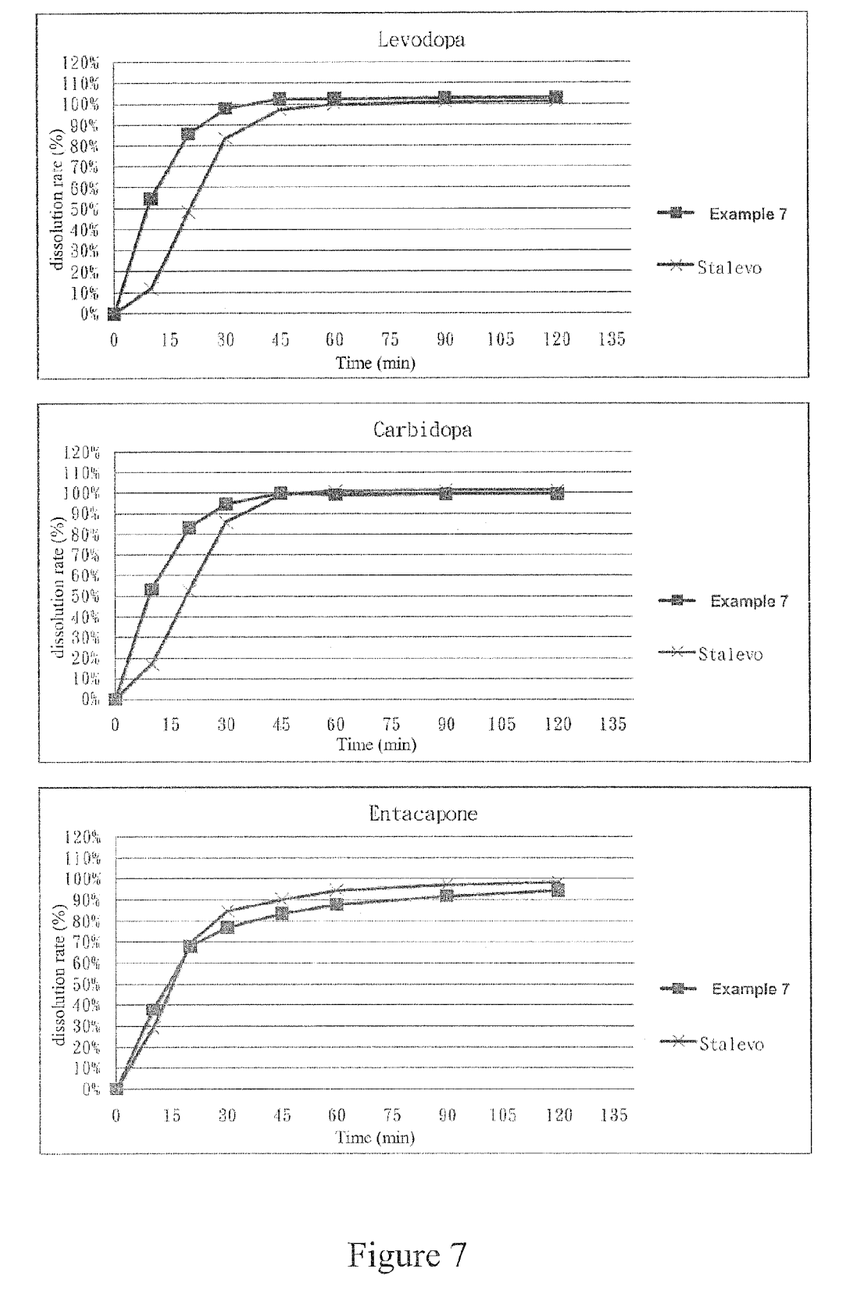
FIG. 7 shows the dissolution profiles of levodopa, carbidopa and entacapone of the tablet obtained from Example 7 in the period of 120 minutes, wherein the reference product is Stalevo®.

Dissolution tests were conducted according to Example 1, and the dissolution profiles of levodopa, carbidopa and entacapone of said tablets in the period of 120 minutes were monitored, wherein Stalevo® was used as a reference product. The result is shown in FIG. 7, wherein the dissolution amounts of levodopa, carbidopa and entacapone are very similar to that of the reference product.

Example 8

First, the ingredients listed in the following Table 22 were wet granulated to obtain granules containing levodopa and carbidopa: 1.4 mg of HPMC E5 LV was dissolved in the water to obtain a 5% HPMC E5 LV solution. Then, remained HPMC E5 LV, carbidopa monohydrate, levodopa and mannitol were sequentially and evenly mixed to obtain a first mixture. After that, said first mixture and said 5% HPMC E5 LV solution were sequentially introduced into a granulator and granulated. The resulted granules were sieved through a 25 mesh sieve and then dried in a 50° C. oven until the water content thereof is between the range of 1%-3%. A first granule is therefore obtained.

TABLE 22

| ingredients | weight(mg) |
| --- | --- |
| Levodopa | 100.00 |
| Carbidopa monohydrate | 27.00 |
| mannitol | 88.00 |
| HPMC E5 LV | 16.40 |
| Total weight | 231.40 |

Next, the ingredients listed in the following Table 23 were wet granulated to obtain granules containing entacapone: microcrystalline cellulose, SDS, mannitol, PVP K30 and entacapone was sequentially and evenly mixed to obtain a second mixture. After that, said second mixture was sieved through a 100 mesh sieve and the sieved powder was put into a granulator, sprayed with deionized water, and granulated. The resulted granules were sieved through a 25 mesh sieve and then dried in a 50° C. oven until the water content thereof is between the range of 1%-3%. A second granule is therefore obtained.

TABLE 23

| ingredients | weight(mg) |
| --- | --- |
| Entacapone | 200.00 |
| microcrystalline cellulose | 0.50 |
| mannitol | 88.00 |
| PVP K30 | 120.00 |
| SDS | 20.00 |
| Total weight | 428.50 |

Last, tablets were prepared according to the ingredients listed in the following Table 24: said first granules containing levodopa and carbidopa were mixed with 1.7 mg of magnesium stearate to obtain a first mixture; said second granules containing entacapone were mixed with 5 mg of crospovidone and 3.4 mg of magnesium stearate to obtain a second mixture; then, said first mixture and said second mixture were compressed into a double-layer tablet.

TABLE 24

| ingredients | weight(mg) |
| --- | --- |
| first granule | 231.40 |
| second granule | 428.50 |
| crospovidone | 5.00 |
| magnesium stearate | 5.10 |
| Total weight | 670.00 |

Figure 8:
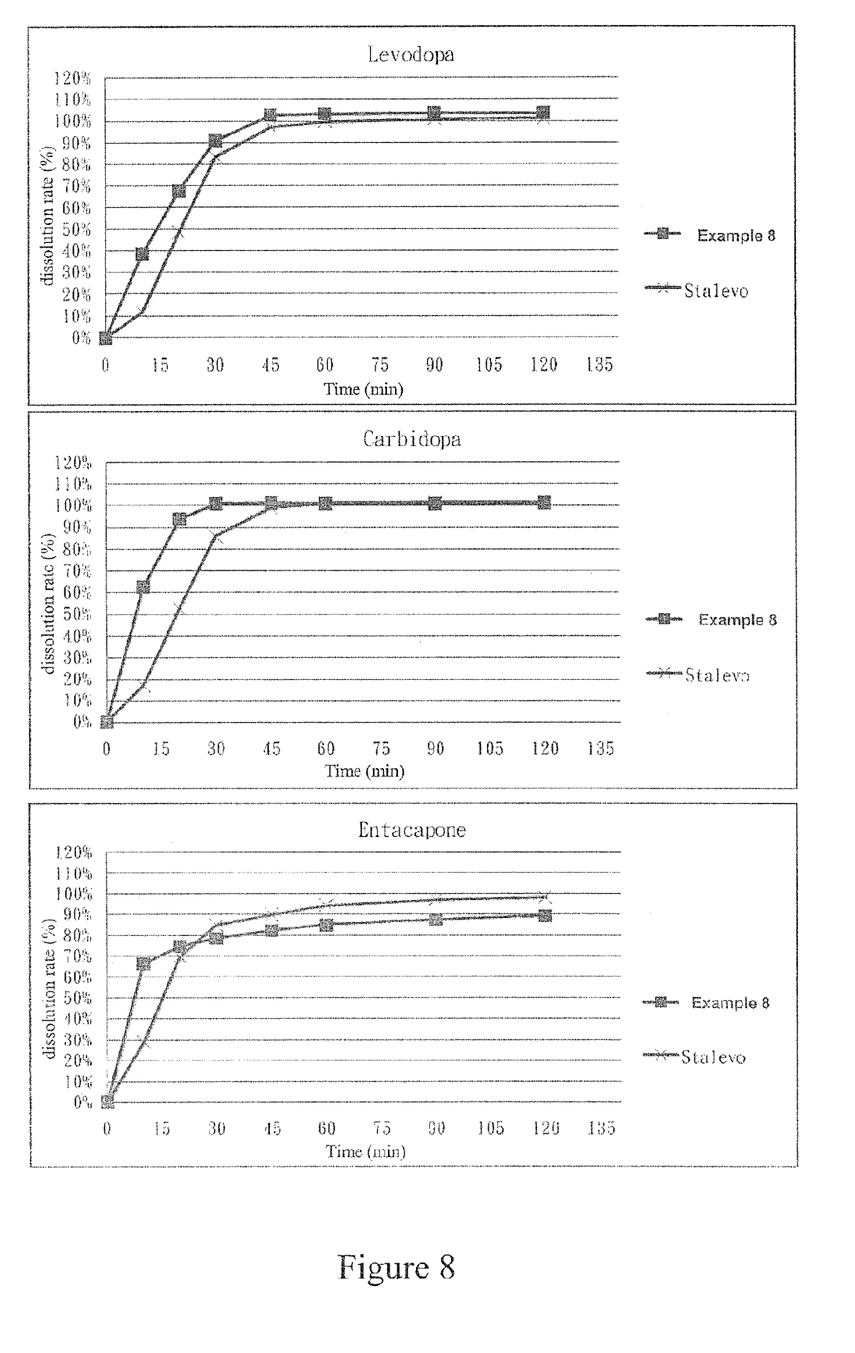
FIG. 8 shows the dissolution profiles of levodopa, carbidopa and entacapone of the tablet obtained from Example 8 in the period of 120 minutes, wherein the reference product is Stalevo®.

Dissolution tests were conducted according to Example 1, and the dissolution profiles of levodopa, carbidopa and entacapone of said tablets in the period of 120 minutes were monitored, wherein Stalevo® was used as a reference product. The result is shown in FIG. 8, wherein the dissolution amounts levodopa, carbidopa and entacapone are very similar to that of the reference product.

What is claimed is:

1. An oral solid pharmaceutical composition for treating Parkinson's disease, comprising first granules that comprise 25-300 milligrams of levodopa and 5-75 milligrams of carbidopa but that do not comprise entacapone, and
    second granules that comprise a binder that binds particles
        which comprise sodium dodecyl sulfate (SDS) and 25-300 milligrams of entacapone,
        which do not comprise levodopa or carbidopa, and
        which comprise entacapone particles having a diameter of at least about 150 micrometers,
wherein
    the size of the particles,
    the identity of the binder, and
    the amounts of the binder, entacapone, and SDS in the second granules are selected such that when the composition is assessed using a modification of USP levodopa/carbidopa/entacapone dissolution method USP 32, NF27 (1791) in which the USP standard basket with a rotation speed of 125 rotations per minute and 900 milliliters of pH 5.5 phosphate buffer solution are used, the time required for 90% of the entacapone to dissolve in the buffer solution is greater than about 25 minutes, but not more than about 80 minutes.

2. The composition of claim 1, being in the form of a tablet.

3. The composition of claim 1, being in the form of a double-layer tablet.

4. A method for preparing an oral solid pharmaceutical composition for treating Parkinson's disease, the method comprising
    (a) mixing levodopa, carbidopa and a first excipient to obtain a first mixture;
    (b) granulating the first mixture to obtain first granules that do not contain entacapone;
    (c) mixing entacapone, a binder, and SDS to obtain a second mixture;
    (d) granulating the second mixture to obtain second granules in which the binder binds particles
        which comprise entacapone and SDS,
        which do not comprise levodopa or carbidopa, and
        which comprises entacapone particles having a diameter of at least about 150 micrometers;
    wherein
        the size of the particles,
        the identity of the binder, and
        the amounts of the binder, entacapone, and SDS in the second granules
            are selected such that when the composition is assessed using a modification of USP levodopa/carbidopa/entacapone dissolution method USP 32, NF27 (1791) in which the USP standard basket with a rotation speed of 125 rotations per minute and 900 milliliters of pH 5.5 phosphate buffer solution are used, the time required for 90% of the entacapone to dissolve in the buffer solution is greater than about 25 minutes, but not greater than about 80 minutes and
    (e) compressing first and second granules into a tablet.

5. The method of claim 4, wherein said step (e) is compressing the first granules into one layer and the second granules into the other layer of a double-layer tablet.

6. The method of claim 4,
    wherein the first granules comprise an excipient selected from the group consisting of mannitol, a sugar, a starch, and a hydroxypropyl methylcellulose, and
    wherein the binder is selected from the group consisting of polyvinyl pyrrolidone (PVP), a starch, and a microcrystalline cellulose.

7. The method of claim 4, wherein each of the first and second mixtures is wet granulated.

8. The method of claim 4, further comprising coating the tablet with a film.

9. The composition of claim 3, wherein the first and second granules are present in different layers of the double-layer tablet.

10. The composition of claim 1, wherein the first granules comprise a combination of one or more excipients
    that are mixed with the levodopa and the carbidopa and
    that are selected such that when the composition is assessed using a modification of USP levodopa/carbidopalentacapone dissolution method USP 32, NF27 (1791) in which the USP standard basket with a rotation speed of 50 rotations per minute and 750 milliliters of 0.1 normal hydrochloric acid are used, the dissolution rates of the levodopa and the carbidopa are such that
        the time required for 90% of the levodopa to dissolve in the acid is greater than about 10 minutes, but not greater than about 65 minutes and
        the time required for 90% of the carbidopa to dissolve in the acid is greater than about 10 minutes, but not greater than about 65 minutes.

11. The composition of claim 10, wherein
    the time required for 90% of the entacapone to dissolve in the buffer solution is about 45 minutes,
    the time required for 90% of the levodopa to dissolve in the acid is about 35 minutes, and
    the time required for 90% of the carbidopa to dissolve in the acid is about 35 minutes.

12. The composition of claim 1, wherein the binder is povidone.

13. The composition of claim 12, wherein the second granules further comprise microcrystalline cellulose and mannitol.

14. The composition of claim 12, wherein the second granules further comprise microcrystalline cellulose and lactose.

15. The composition of claim 14, wherein the relative proportions, by weight, of entacapone:SDS:povidone:microcrystalline cellulose:mannitol in the second granules are about 200:12:40:0.5:168.

16. The composition of claim 1, wherein the first granules further comprise an excipient selected from the group consisting of binders, diluents, disintegrants, lubricants, compression aid agents, preservatives, coating agents, flavors, colors, and sweeteners.

17. The composition of claim 1, wherein the first granules further comprise a binder and a diluent.

18. The composition of claim 16, wherein the binder is hydroxypropyl methylcellulose (HPMC) and the diluent is mannitol.

19. The composition of claim of claim 18, wherein the carbidopa is present in the form of carbidopa monohydrate and the relative proportions, by weight, of levodopa:carbidopa monohydrate:mannitol:HPMC in the first granules are about 100:27:88:16.4.

20. The composition of claim 1, wherein, in addition to the first and second granules, the composition further comprises an excipient independently selected from the group consisting of binders, diluents, disintegrants, lubricants, compression aid agents, preservatives, coating agents, flavors, colors, and sweeteners.

21. The composition of claim 20, being in the form of a tablet and comprising the first granules, the second granules, a disintegrant, and a lubricant.

22. The composition of claim 20, being in the form of a tablet and comprising the first granules, the second granules, crospovidone, and magnesium stearate.

* * * * *